United States Patent
Lepple-Wienhues

(10) Patent No.: US 10,307,048 B2
(45) Date of Patent: Jun. 4, 2019

(54) OTOSCOPE AND OTOSCOPIC METHOD BASED ON SPECTRAL ANALYSIS

(71) Applicant: Helen of Troy Limited, Belleville, St. Michael (BB)

(72) Inventor: Albrecht Lepple-Wienhues, Pontarlier (FR)

(73) Assignee: Helen of Troy Limited, Belleville (BB)

( * ) Notice: Subject to any disclaimer, the term of this patent is extended or adjusted under 35 U.S.C. 154(b) by 24 days.

(21) Appl. No.: 15/307,781

(22) PCT Filed: May 5, 2015

(86) PCT No.: PCT/EP2015/000915
§ 371 (c)(1),
(2) Date: Oct. 28, 2016

(87) PCT Pub. No.: WO2015/169436
PCT Pub. Date: Nov. 12, 2015

(65) Prior Publication Data
US 2017/0049310 A1    Feb. 23, 2017

(30) Foreign Application Priority Data

May 5, 2014    (WO) .................. PCT/EP2014/001195

(51) Int. Cl.
*A61B 1/227*    (2006.01)
*A61B 1/00*    (2006.01)
(Continued)

(52) U.S. Cl.
CPC .......... *A61B 1/227* (2013.01); *A61B 1/00009* (2013.01); *A61B 1/00057* (2013.01);
(Continued)

(58) Field of Classification Search
CPC . A61B 1/227; A61B 1/00009; A61B 1/00057; A61B 1/05; A61B 1/0638;
(Continued)

(56) References Cited

U.S. PATENT DOCUMENTS 6,110,106 A * 8/2000 MacKinnon et al. .......................
                                              A61B 5/0071
                                                  600/160
8,115,934 B2 * 2/2012 Boppart et al. ...... A61B 5/0066
                                                  356/479
(Continued)

FOREIGN PATENT DOCUMENTS

CN    101984915 A    3/2011
JP    2004535834 A   12/2004
(Continued)

OTHER PUBLICATIONS

International Search Report, dated Jul. 23, 2015, for International Application No. PCT/EP2015/000915, 6 pages.

*Primary Examiner* — Pedro Philogene
*Assistant Examiner* — David C Comstock
(74) *Attorney, Agent, or Firm* — Dinsmore & Shohl LLP

(57) ABSTRACT

An otoscope device is disclosed comprising a portion configured to be introduced in an ear canal of a patient's outer ear; and an electronic imaging unit configured for capturing at least one image of the patient's outer ear, especially of the eardrum. The otoscope device further comprises electronic and/or optic means configured for determining spectral information, especially with respect to wavelengths shorter than 550 nm; and is configured for identifying and/or locating objects shown in the at least one image, especially the eardrum, in dependence on a specific amount of blue components and/or UV components of the image or of radiation reflected from the object. Further, a method is
(Continued)

disclosed for identifying and/or locating objects in a subject's ear or to a method of identifying an eardrum.

26 Claims, 4 Drawing Sheets

(51) Int. Cl.
    *A61B 1/05*    (2006.01)
    *A61B 1/06*    (2006.01)
    *A61B 5/00*    (2006.01)
    *A61B 5/12*    (2006.01)
(52) U.S. Cl.
    CPC .............. *A61B 1/05* (2013.01); *A61B 1/0638* (2013.01); *A61B 1/0684* (2013.01); *A61B 5/0075* (2013.01); *A61B 5/0084* (2013.01); *A61B 5/12* (2013.01); *A61B 5/6815* (2013.01); *A61B 5/6817* (2013.01)
(58) Field of Classification Search
    CPC ... A61B 1/0684; A61B 5/0075; A61B 5/0084; A61B 5/12; A61B 5/6815; A61B 5/6817
    USPC ........................................................ 600/200
    See application file for complete search history.

(56) References Cited

U.S. PATENT DOCUMENTS

| | | | |
|---|---|---|---|
| 8,617,061 | B2 | 12/2013 | Magalhães et al. |
| 2004/0158157 | A1 | 8/2004 | Jensen et al. |
| 2005/0228231 | A1* | 10/2005 | MacKinnon ............. A61B 1/05 600/180 |
| 2006/0282009 | A1 | 12/2006 | Oberg et al. |
| 2011/0026037 | A1* | 2/2011 | Forster .................. A61B 1/227 356/601 |
| 2013/0289353 | A1 | 10/2013 | Seth et al. |
| 2015/0044098 | A1* | 2/2015 | Smart .................. A61B 5/0013 422/82.05 |
| 2015/0351637 | A1* | 12/2015 | Ruppersberg ...... A61B 1/00179 600/474 |

FOREIGN PATENT DOCUMENTS

| | | |
|---|---|---|
| JP | 2006084425 A | 3/2006 |
| JP | 2014505494 A | 3/2014 |
| JP | 2015530886 A | 10/2015 |
| WO | 2007049562 A1 | 5/2007 |
| WO | 2009/157825 A1 | 12/2009 |
| WO | 2014117954 A2 | 8/2014 |

* cited by examiner

US 10,307,048 B2

OTOSCOPE AND OTOSCOPIC METHOD BASED ON SPECTRAL ANALYSIS

BACKGROUND

Technical Field

The present disclosure relates to an otoscope device, especially configured to be manipulated by a user during its application, comprising a portion configured to be introduced in an ear canal of a patient's outer ear; and an electronic imaging unit configured for capturing at least one image of the patient's outer ear, especially of the eardrum. The present disclosure also relates to a method of identifying and/or locating objects in a subject's ear, comprising the steps: providing an electronic imaging unit; capturing at least one image of the patient's outer ear, especially of the eardrum; determining spectral information to identify objects shown in the at least one image by electronic and/or optic means, especially in order to identify a healthy eardrum. In particular, the present disclosure relates to an otoscope device according to claim 1 as well as to a method of identifying and/or locating objects in a subject's ear or to a method of identifying an eardrum according to one of the respective independent method claim.

Description of the Related Art

Looking into ears is called "otoscopy". Otoscopy is a standard medical examination technique established more than 100 years ago. Medical students learn otoscopy early in their studies during the practical course in physiology. Otoscopic examination assists the skilled physician in examining the ear canal or eardrum which may be affected, e.g., by otitis media (OM), otitis media with effusion (OME), otitis externa, and eardrum perforation. OME is defined by the presence of middle ear effusion, i.e., a liquid behind an intact tympanic membrane (eardrum) without signs or symptoms of acute infection. OME is one of the most frequent pediatric diagnoses. Object recognition in otoscopy is also directed to the identification of particles or any material, e.g., hair, earwax, foreign objects, etc., which may obstruct the ear canal or coat the eardrum. Such applications are highly desired for routine care.

For any application of an otoscope or its mode of use, it is desired to allow its user to distinguish the objects located in the ear canal or at its end, in particular the eardrum itself of any objects adhering to the eardrum.

Reliably and securely handling an otoscope of the art is currently subject to only well trained physicians and not amenable to the larger community of practitioners. In particular, with an otoscope of the art, reliable identification of objects within the ear canal may only be carried out by well-trained physicians. A study published in the US as a result of a survey has shown that even physicians often fail to (correctly) determine the status of, e.g., the subject's eardrum or fail to correctly interpret the image provided by the otoscope (i.e., correct and meaningful object recognition). Such failures result in misinterpretation of the status of the inner ear canal or the eardrum. As a consequence, e.g., over-medication with antibiotics for treating supposed inflammations of the eardrum occurs, because physicians tend to err on the side of caution, or meaningless image interpretation occurs.

The otoscopic methods known in the art are—as a matter of fact—subject to well-trained physicians which are capable of interpreting images captured within the ear canal, especially in order to carry out diagnosis. In dependence on the content of the captured images, the physician usually has to adjust the otoscope, such as illumination or a relative position of the otoscope within the ear canal.

Consequently, until today otoscopy has almost exclusively been applied by well-trained medical doctors. However, it would be desirable to provide an otoscope which assists in determining/discerning different objects within the ear canal more reliably. Also, it would be desirable to extend the capability of otoscopy beyond the trained professionals. Due to its broad spectrum of applications, it should be made amenable to any layperson, such as parents, who may desire to, e.g., examine whether dirt or particles is/are located in the children's ear canal. Also, during childhood, otitis media (OM) or otitis media with effusion (OME) may occur several times. Thus, otoscopy should be made amenable to parents which are not skilled at all, at least in order to carry out a kind of pre-diagnosis, or to assess a likelihood of inflammation of the eardrum. The parents should be provided with information which facilitates their decision if it is required to visit a physician. Any more advanced or final disease diagnosis may be carried out by the physician.

U.S. Pat. No. 8,617,061 B2 describes a device for measuring and analyzing the color of the outer ear and ear canal, wherein a tri-color emitter and a tri-color sensor are provided in conjunction with optical fibers for conducting emitted and reflected light, respectively, wherein emission of light by the emitter is independently controlled in its three components. The tri-color sensor is adapted to an existing otoscope. U.S. Pat. No. 8,617,061 aims for an objective measurement of red shifted color reflection in case of inflammation in the ear. U.S. Pat. No. 8,617,061, however, does not address the aforementioned problem of needing a trained specialist to perform the procedure, nor does it address the challenge of identifying and/or locating the eardrum in order to gain clinical relevant information from that structure. U.S. Pat. No. 8,617,061 also fails to obtain spatial information about the spectral properties of reflected light. E.g., reflected light with a red shift collected into a light guide could originate either from a reddish eardrum or from a reddish ear canal.

It is one object of the present disclosure to provide a device, especially an otoscope, configured for electronically identifying and/or locating objects in a subject's ear in a reliable way, the device/otoscope preferably being provided for use by laypersons without special training. It is a further object of the present disclosure to provide a method of identifying and/or locating objects, especially the eardrum, in a subject's ear in a reliable way. The object may also be described as accurately characterizing a specific object, once the object has been identified and/or located.

BRIEF SUMMARY

In particular, at least one of the above mentioned objects is achieved by an otoscope device, especially configured to be manipulated by a user during its application, comprising: a portion configured to be introduced in an ear canal of a patient's outer ear; and an electronic imaging unit configured for capturing at least one image of the patient's outer ear, especially of the eardrum, especially based on reflected radiation of radiation emitted by at least one source of radiation; wherein the otoscope device further comprises electronic and/or optic means, especially a logic unit, configured for determining spectral information or configured for analysis of the at least one image, especially with respect to wavelengths shorter than 550 nm, and configured for identifying and/or locating objects shown in the at least one image, especially the eardrum, in dependence on a specific amount of blue components and/or UV components of the image or of radiation reflected from the object. In particular, the electronic and/or optic means are configured for identifying and/or locating objects in dependence on a spectral composition of the at least one image or a pixel or a pixel area of the image which exhibits a specific minimum amount of specific spectral components, especially a specific minimum amount of blue spectral components or spectral components having wavelengths shorter than 550 nm, preferably shorter than 480 nm. Preferably, color information, especially with respect to blue colors, is evaluated. Color information may be evaluated within an acquired image and/or with respect to reflected radiation.

Thereby, evaluation of an image can be carried out in order to accurately locate several objects within the ear canal. Also, a condition, especially a medical condition of a specific object may be determined. Preferably, the eardrum is identified. Nonetheless, also, other objects, e.g., tissue confining the ear canal, may be determined, especially indirectly. In case a specific object (i.e., a specific part or section of the captured image) does not exhibit any spectral components in the range of wavelengths of blue light and/or in the range of wavelengths of UV radiation, likelihood is high that this object or section of the ear canal is just not the eardrum.

The range of 480 nm to 500 nm may be understood as any range which is appropriate for delimiting blue light or UV radiation from radiation having longer wavelengths, e.g., green light (ca. 480 nm to 560 nm), yellow light (ca. 560 nm to 580 nm), orange light (ca. 580 nm to 630 nm) or red light (ca. 630 nm to 790 nm).

The wording "amount of spectral components" preferably refers to a specific portion of spectral components.

The electronic imaging unit may comprise, e.g., a Bayer filter, i.e., a color filter array.

The electronic and/or optic means may comprise a logic unit or processing unit configured for determining/identifying an object in dependence on a specific composition of spectral components, especially in dependence on a specific threshold value of a degree/amount/ratio/percentage of blue components.

The present disclosure is based on the finding that identification or localization of an object, especially the eardrum, may be complicated or hampered essentially by two factors, namely excessive radiation (intensity of radiation which is too high) and/or evaluation of reflections without any reference to localization. In fact, because of the ear canal's geometry, reflections captured by an otoscope may originate from a plurality of different sections of the ear, e.g., due to multiple reflections of the same radiation within the ear canal. Referring to blue/UV spectral components may reduce these effects, which allows for facilitating spectral analysis.

The present disclosure is based on the further finding that the different tissues within the ear canal, especially the eardrum, exhibit very individual tissue properties having individual optical reflection properties. Reflections of light or near visible radiation may be evaluated in order to determine each individual object, especially the eardrum. In other words: Spectral analysis may be carried out not (only) for assessing a specific color, but also for identifying and/or locating different objects, especially for accurately identifying and/or locating the eardrum. Thereby, according to one aspect, also a likelihood of an inflammation of the eardrum can be determined, especially after locating the eardrum area using reflective spectral properties.

The present disclosure is also based on the finding that the properties of the tissue of the eardrum can be evaluated in order to reliably identify a healthy eardrum or transparent sections of an inflamed eardrum. It has been found that an eardrum reflects light or invisible radiation having a specific spectral composition which differs from the spectral composition reflected by tissue surrounding the eardrum. In particular, it has been found that visible or near visible radiation reflected by a healthy eardrum exhibits a spectral composition which is substantially characterized by wavelengths in the spectrum of UV radiation or in the spectrum of blue light, i.e., wavelengths which are shorter than 550 nm or 500 nm, especially shorter than 480 nm to 500 nm or even shorter than 450 nm. In contrast, light reflected by tissues surrounding the eardrum, e.g., tissue confining the ear canal, exhibits a spectral composition which is predominantly characterized by wavelengths in the spectrum of red light, i.e., wavelengths which are considerably longer than 500 nm or 550 nm or even 600 nm, especially up to 780 nm. In other words: It has been found that the eardrum exhibits tissue properties which considerably differ from tissue properties of surrounding tissue, and that these differences may be evaluated in order to reliably identify the eardrum, or even in order to medically/clinically characterize the eardrum, i.e., to determine a medical condition of the eardrum.

The present disclosure is also based on the finding that an eardrum is a relatively thin tissue, having a thickness corresponding to a few layers of cells and fibers only. In certain areas of the eardrum, blood vessels that may provide any reflections in the red spectrum are scarce or not present at all. In particular, the mean thickness is in the range of approximately, e.g., 40 μm, 50 μm or 120 μm in the central region of the eardrum. Further, it has been found that some areas of an eardrum, e.g., the pars tensa, exhibit a very low reflection coefficient of red or green radiation as compared to blue or UV radiation. In contrast, the reflectance of tissues and matter other than the eardrum, especially tissues like skin tissue or matters like earwax, exhibit a different spectral reflection composition, namely a high reflection coefficient of green and/or red spectral components when compared to blue or UV components. Such other tissues may exhibit a higher reflectance for wavelengths longer than ca. 500 nm as compared to a reflectance for wavelengths shorter than ca. 480 nm or 500 nm. Therefore, evaluating blue spectral components and/or UV spectral components within reflected radiation may improve reliable assessment or identification of the eardrum. Further, it has been found that some parts of the eardrum, especially the pars flaccida or the parts attached to the malleus handle, may also reflect preferably in the green/red spectrum. Therefore, spectral analysis of a color image may reveals typical patterns which allow for identifying and locating the eardrum.

The present disclosure is also based on the concept that the eardrum may be reliably identified based on a completely different spectral response as compared to surrounding tissue. Surrounding tissue provides a spectral reflection mainly characterized by long wavelengths (red light), whereas the tissue of the eardrum provides a spectral reflection mainly characterized by short wavelengths (blue light). In the range/spectrum of visible light (color spectrum), the blue color and the red color are arranged on opposite ends of the spectrum. In other words: the difference in wavelength or ratio of intensity of reflections of these two colors is at a maximum. Therefore, identification of the eardrum based on analysis of spectral components having wavelengths shorter than 500 nm, preferably shorter than 480 nm, as compared to longer wavelengths may be carried out reliably.

Further, it has been found that in case the intensity of illumination is high, reflectance of mucosa lining the middle ear located behind the eardrum may dominate the spectrum of reflected radiation. Mucosa is essentially red in appearance, especially when the intensity of illumination is high. Therefore, especially in order to achieve high evaluation accuracy, the intensity of illumination may be adjusted when performing spectral analysis.

In otoscopes used by trained specialists, the light intensity can be typically adjusted between dark and a certain maximal intensity. Therefore, the illumination intensity is not standardized. The perceived spectral composition of the reflected light may be influenced by the chosen intensity. E.g., when the semitransparent eardrum is observed at low illumination levels using a white light source, the eardrum may appear dark to blueish. When the intensity of illumination is increased the eardrum may appear reddish because of the reflected red light from the mucosal walls behind the eardrum lining the middle ear cavity.

The present disclosure is also based on the finding that a radiation (especially light) reflection mechanism within the eardrum differs from reflection mechanisms within tissue surrounding the eardrum. In particular, a major reflection mechanism of the semitransparent parts of the eardrum is Rayleigh scattering, whereas the predominant reflection mechanism within tissue surrounding the eardrum is Mie scattering. Rayleigh scattering may be caused by molecular components within the optically transparent thin membrane. These components include collagen fibers, organelle and cellular membrane layers, as well as cytoplasmic and extracellular molecules. In contrast, Mie scattering is the predominant scatter due to hemoglobin-packed erythrocytes and opaque cellular and extracellular particles. In mucosa, skin, etc., short wavelengths will be absorbed almost completely, especially due to multiple scattering and light path extension. In other words: It has been found that due to the tissue properties of parts of the eardrum, the spectral composition of radiation reflected by the eardrum differs considerably from the spectral composition of radiation reflected by any other tissue or object/matter within the ear canal, especially in case the spectral composition of the source of illumination contains major components in the spectrum of wavelengths shorter than 500 nm to 480 nm or is adjusted with respect to this spectrum. The present disclosure is also based on the concept that the eardrum may be reliably identified and/or located based on evaluation of these different reflection mechanisms. Thus, based on analysis of the spectral composition, identification of the eardrum, especially identification of a healthy eardrum, can be carried out in a reliable way, preferably with respect to the spectrum of wavelengths shorter than 500 nm or 480 nm, especially the blue color spectrum of visible radiation (blue light), especially in comparison with the spectrum of wavelengths longer than 500 nm.

The present disclosure is also based on the finding that in a second step, once the eardrum has been identified and/or located, an inflammation index characterizing the eardrum may be determined from a previously defined area. An assessment of the immediate vicinity of a previously located eardrum area regarding spectral reflection properties is suited to perform a diagnosis. An inflamed eardrum usually exhibits a greater thickness that a healthy eardrum. Blood capillaries are widened and immune system cells are present. Therefore, under these conditions, reflection spectra may shift away from the short wavelengths towards longer wavelengths, and the ratio of reflected radiation changes, e.g., the blue to red ratio decreases. Also, an effusion behind the transparent eardrum is showing typically a color change due to mucus containing immune cells and cell debris. In this context, it has been found that assessment of a likelihood of inflammation may be carried out depending on a specific level of illumination/radiation, in particular based on a minimum level of illumination/radiation, in order to reduce stray light reflected by surrounding tissues. As surrounding tissues usually will reflect red light, reducing the level of illumination/radiation may facilitate determination of red spectral components which are reflected by the eardrum. Reducing the level of illumination/radiation may allow for reliably evaluating a spectral ratio of the eardrum. In particular, only those red spectral components are evaluated which are reflected from the same region from which blue spectral components are reflected. Only those spectral ratios are evaluated which are characterizing the vicinity of the region which exhibits a high ratio of blue spectral components with respect to red spectral components.

The present disclosure is also based on the finding that in a second or further step, an index for a likelihood of OM or OME may be determined, in order to provide the user with an advice for further consultation by a physician.

Determining spectral information may refer to analysis of reflected radiation, especially bluish or blue radiation, and/or analysis of at least one image, especially bluish or blue spectral components of the image, once the image has been acquired. The "ratio of blue to red" may likewise refer to a ratio of UV spectral components to red components. As an image may be conceived as a spatially resolved measurement of reflected radiation, the present disclosure may refer to spectral analysis of reflected radiation both directly within reflected radiation and within an acquired image.

The expression "otoscope device" preferably has to be understood as any device which may function as an otoscope. The otoscope device is not necessarily provided in the form of a manual otoscope. For example, the otoscope device may be integrated in a medical device comprising several devices or fulfilling several functions.

The expression "light" preferably has to be understood as visible radiation in the range of 380 nm to 780 nm or even 1000 nm. The expression "radiation" preferably has to be understood as visible or invisible radiation in the range of 10 nm to 780 nm, wherein X-radiation preferably is not comprised. The expression "UV radiation" preferably has to be understood as invisible radiation in the range of 10 nm to 380 nm, especially 100 nm to 380 nm. The expression "UV components" preferably has to be understood as any spectral components of radiation in the range of 10 nm to 380 nm, or respective image information.

The expression "spectrum" or "spectral composition" preferably refers not only to the visible light spectrum, but also to the electromagnetic spectrum comprising wavelengths shorter than visible light.

The expression "red spectral component" or "blue spectral component" preferably refers not only to properties of emitted or reflected light, but also to color information within a captured image.

The composition of the eardrum may be classified in three layers:
 1. core of collagenous connective tissue;
 2. outer covering of stratified squamous epithelium (SSE);
 3. inner covering of simple cuboidal epithelium (SCE), the inner covering facing the middle ear cavity.

It has been found that by spectral analysis, each of these layers may be identified for identifying, characterizing and/ or locating the eardrum, especially as all these layers contain scarce or no blood vessels, except in the pars flaccida and the region of the malleus handle.

According to one embodiment of the disclosure, the otoscope further comprises at least one source of radiation configured for radiating the ear canal. By means of a source of radiation, especially a source of radiation emitting UV radiation and/or blue light, the eardrum may be identified and analyzed more efficiently and more reliably.

The expression "source of radiation" preferably has to be understood as a source emitting UV radiation and/or light, or as a source of radiation in conjunction with at least one guide of radiation, e.g., an optical fiber or a fiber for guiding UV radiation.

A "guide of radiation" preferably has to be understood as any means for guiding radiation, especially blue light from a first point towards a second point. According to one embodiment, the guide of radiation is a light guide.

According to one embodiment of the disclosure, the at least one source of radiation is configured for emitting blue light and/or UV radiation, especially in the range of 550 nm to 10 nm, preferably below 480 nm. Such a source of radiation facilitates identification and analysis of the eardrum. Preferably, the at least one source of radiation is configured for not emitting radiation or light having wavelengths in the range above 550 nm or 600 nm. Preferably, the at least one source of radiation is configured for only emitting radiation having wavelengths shorter than red or orange light, especially shorter than 580 nm or 560 nm.

According to one embodiment of the disclosure, the at least one source of radiation is a source of radiation with a specific spectral maximum in the spectrum of visible light below 500 nm, preferably below 480 nm, especially an LED with a spectral maximum in the spectrum of blue light between 380 nm and 500 nm, especially 420 nm and 480 nm. The LED may be provided in the form of a white (preferably cold white) LED. Thereby, red spectra of emitted light can be minimized. Light reflections of red (especially highly vascularized) tissue can be minimized.

According to one embodiment of the disclosure, the electronic and/or optic means are configured for adjusting the spectral composition of radiation emitted by the at least one source of radiation, especially with respect to a specific wavelength below 550 nm, preferably below 480 nm, in particular with respect to a spectral maximum within the spectrum of 380 nm to 500 nm, especially 420 nm to 480 nm. Adjusting the spectral composition of emitted radiation may further improve reliability of identification of the eardrum. In particular, a first image may be captured during emission of radiation with a relatively broad spectrum, and a second or further image may be captured during emission of UV radiation or blue light. These images may be compared or analyzed in conjunction with each other.

According to one embodiment of the disclosure, the electronic and/or optic means are configured for calibration of the spectral composition of radiation emitted by the at least one source of radiation, and for comparing a determined spectral composition of reflected radiation with the calibrated spectral composition of emitted radiation. Such electronic and/or optic means allow for reliably identifying and/or locating objects, especially the eardrum. In particular, it may be determined accurately which spectral components have been absorbed by tissue/objects within the ear canal, and which spectral components are reflected spectral components. Calibration may also be carried out with respect to brightness or an intensity of radiation.

Accordingly, the present disclosure may also relate to a method comprising calibrating a spectral sensitivity of the electronic imaging unit and/or calibrating the spectral composition of the at least one source of radiation and/or brightness of the at least one image. Calibration allows for more reliable analysis of the spectral composition of reflected radiation, and thus, more reliable identification of objects. It has been found that in case the light intensity is very high allowing light for passing through a healthy eardrum, which is semitransparent, a considerable amount of light within the red spectrum may be reflected by the tympanic cavity (especially due to illumination of red mucosa confining the middle ear). Thus, calibrating the brightness of the image or calibrating the intensity of emitted radiation enables more accurate evaluation of the (absolute) degree of red channel reflection and its source. In other words, spectral calibration of an imaging sensor in combination with spectral calibration of illumination means allows for more accurate evaluation of the tissue types and conditions.

In particular, with a method comprising calibration, any (actual) varying voltage of any batteries of an otoscope for carrying out the method does not imply or implicate any source of error. Using traditional otoscopes, it is likely that at low voltage, the spectrum of the illumination is shifted towards the red spectrum, i.e., less energy intensive wavelength, especially when using halogen light bulbs. Calibrating the spectral range and/or the intensity of illumination/radiation facilitates absolute spectral analysis. In other words: the electronic imaging unit can be provided with a calibrated color balance.

Calibration can be carried out, e.g., based on feedback illumination control with respect to different objects or different kinds of tissue, once the respective object or tissue has been identified. Thereby, spectral norm curves with respect to different light intensities may provide further data based on which calibration may be carried out.

According to one embodiment of the disclosure, the electronic and/or optic means are configured for analyzing the amount of blue components and/or UV components of reflected radiation with respect to the spectral composition of emitted radiation. Referring to the spectrum of emitted radiation may provide higher accuracy. Also, accuracy is independent of any specific type of source of radiation. In other words: Referring to the spectrum of emitted radiation allows for replacing the source of radiation, e.g., in case the source of radiation is inoperative or does not work anymore. Even in case the source of radiation is (erroneously) replaced by another type of source of radiation, accuracy can be ensured. Further, accuracy is independent of any (actual) varying voltage of any batteries of the otoscope device.

According to one embodiment of the disclosure, the electronic and/or optic means are configured for adjusting the intensity of radiation of the at least one source of radiation, especially configured for reducing the intensity of radiation in case the at least one image exhibits a spectral composition which exceeds a specific maximum amount of spectral components having wavelengths longer than 550 nm, especially of red spectral components. As described above, in case the intensity of radiation allows radiation for passing through the eardrum, a considerable amount of radiation within the red spectrum may be reflected by the tympanic cavity. Thus, reducing the intensity/brightness such that radiation does not pass through the eardrum (or such that essentially all radiation is reflected by the eardrum, and not by any tissue behind the eardrum) enables more accurate evaluation of the (absolute) degree of red channel reflections and its source.

According to one embodiment of the disclosure, the electronic and/or optic means are configured for adjusting the intensity of radiation of the at least one source of radiation with respect to specific spectral components of emitted light/radiation. The intensity of radiation may be adjusted within the spectrum of blue light, especially without varying the intensity of radiation of any other spectral components different than blue light or UV radiation. Thereby, the amount of reflected radiation within a specific spectral range, especially the amount of reflected blue light or UV radiation, may be assessed and evaluated under specific conditions, which may increase accuracy and reliability also.

According to one embodiment of the disclosure, the otoscope device is a manual otoscope configured for manual application, further comprising: a handle portion allowing a user to manipulate the otoscope during its application; and a head portion exhibiting a substantially tapering form extending along a longitudinal axis of the head portion, wherein the head portion has a proximal end adjacent to the handle portion and a smaller distal end configured to be introduced in an ear canal of a patient's outer ear. Preferably, the at least one image is captured by an image sensor which is arranged at the distal tip of the head portion. The image can be captured directly by the imaging unit. It is not required to guide reflected light within any optical fiber in a proximal direction towards a proximal end of the head portion.

According to one embodiment of the disclosure, at least one of the at least one source of radiation and/or the electronic imaging unit respectively is arranged at a distal tip of the otoscope, wherein at least one of the at least one source of radiation and/or the electronic imaging unit respectively is radially offset and/or an visual axis of the at least one source of radiation and/or of the electronic imaging unit respectively is tilted. Such an arrangement allows for capturing images of the eardrum and for radiating (especially illuminating) the eardrum substantially irrespective of the relative position of a head portion of the otoscope within the ear canal. This allows for simplified/facilitated use by laypersons also.

At least one of the above mentioned objects is also attained by an otoscope device comprising electronic and/or optic means configured for determining spectral information of radiation reflected within an ear canal and configured for identifying the eardrum in dependence on a specific amount of blue components and/or UV components detected within the reflected radiation. In other words: Determining spectral information may be carried out directly with respect to reflected radiation, irrespective of any manner/method of image analysis. In particular, it has been found that "blue/bluish color properties" of the eardrum are such a distinctive mark that the eardrum may be identified in a reliable way directly based on analysis of reflected radiation.

At least one of the above mentioned objects is also attained by a method of identifying and/or locating objects in a subject's ear, especially by means of an otoscope device according to any of the preceding claims, comprising the steps:

(S1) providing an electronic imaging unit, especially by introducing the electronic imaging unit into an ear canal of a subject's outer ear;

(S2) capturing at least one image of the patient's outer ear, especially of the eardrum, by means of the electronic imaging unit, especially based on reflected radiation of radiation emitted by at least one source of radiation;

(S3) determining spectral information to identify objects shown in the at least one image by electronic and/or optic means, especially by a logic unit, in order to automatically identify at least one of the objects, especially the eardrum; and (S4) identifying at least one of the objects, especially the eardrum, in dependence on a specific amount of blue components and/or UV components of the image or of radiation reflected from the object, especially in dependence on a spectral composition which exhibits a specific minimum amount of specific spectral components, especially a specific minimum amount of blue spectral components or spectral components having wavelengths shorter than 550 nm, preferably shorter than 480 nm. Such a method provides at least some of the advantages as described in context with the otoscope device. Identifying and/or locating objects may be carried out based on/in dependence on the spectral composition of the at least one image or a pixel or pixel area of the image.

According to one embodiment of the disclosure, the method further comprises the steps:

(S1a) introducing at least one source of radiation into the ear canal; and (S1b) radiating the ear canal by means of the at least one source of radiation, especially by means of an LED which is configured for emitting blue light and/or by means of a source of radiation which is configured for emitting UV radiation, preferably with radiation having a spectral maximum in the spectrum of blue light. Radiating the ear canal, especially with radiation having a specific spectral composition, may facilitate evaluation of spectral information.

According to one embodiment of the disclosure, spectral information is determined based on a ratio of wavelengths below 550 nm or 480 nm to wavelengths above 550 nm or 600 nm (especially the ratio of blue spectral components to red spectral components), wherein the ratio is evaluated, and wherein a high ratio (corresponding to a high amount of spectral components with wavelengths below 550 nm or 480 nm, especially a high amount of blue light) is evaluated as an indicator for the eardrum, especially for a healthy eardrum. Referring to such a ratio and evaluating the ratio may allow for determining the eardrum more reliably. Evaluating the ratio may allow for distinguishing between a relative amount of short wavelength and an absolute amount of short wavelength.

According to one embodiment of the disclosure, spectral information is determined based on brightness of the at least one image or a pixel or pixel area of the image, especially in dependence on a specific intensity of radiation of emitted and/or reflected radiation. Evaluating reflected radiation in dependence on a specific intensity of illumination may provide more accurate assessment of stray light components or light/radiation reflected by any tissue or liquid behind the eardrum.

According to one embodiment of the disclosure, the spectral information is determined in sections with respect to a specific pixel or pixel area of the at least one image. This allows for pattern recognition and accurate localization of objects within the image. In other words: Identifying and/or locating objects may comprise pattern recognition based on pixels or pixel areas of the at least one image which exhibit a minimum amount of specific spectral components and/or a specific spectral composition, in particular a minimum amount of blue spectral components (especially of blue light) and/or a specific spectral composition (e.g., specific spectral peaks) in the spectrum of wavelengths below 550 nm, especially between 380 nm and 480 nm or 500 nm.

According to one embodiment of the disclosure, the method includes radiating the ear canal, wherein an intensity of radiation is adjusted, especially reduced, to a minimum intensity for acquiring the at least one image. Such a control step allows for more reliably assessing the origin of reflected radiation. Preferably, the electronic and/or optic means are configured to carry out such a control or intensity reduction. Preferably, the intensity of radiation is reduced in case the at least one image exceeds a specific maximum amount of red spectral components, especially in dependence on a specific ratio of blue spectral components to red spectral components.

According to one embodiment of the disclosure, an intensity of radiation is reduced in case the at least one image exceeds a specific maximum amount of spectral components having wavelengths longer than 550 nm, especially red spectral components, especially in dependence on a specific ratio of blue spectral components to red spectral components. Such an adjustment or control may reduce the amount of any stray light.

According to one embodiment of the disclosure, determining spectral information comprises analysis of blue spectral components, wherein identifying the at least one object comprises identifying the eardrum and is carried out in dependence on the amount of blue spectral components, especially relative to the amount of red spectral components. Analyzing the amount of blue spectral components allows for focusing on the tissue properties of the eardrum, in order to better distinguish the eardrum from any surrounding tissue.

According to one embodiment of the disclosure, determining spectral information comprises pixelwise subtraction of red spectral components. This method step allows for specifically analyzing spectral information which may indicate the eardrum or the position of the eardrum.

According to one embodiment of the disclosure, the method further comprises a step of determining a condition, especially a medical condition, of the at least one object in dependence on a spectral composition which exhibits a specific minimum or maximum amount of specific spectral components, especially a specific minimum amount of blue spectral components. Determining threshold values for specific spectral components, especially blue and/or red components, allows for an easy method for automatically identifying specific objects, especially the eardrum. Any sophisticated, quite complicated algorithm is not necessarily required.

According to one embodiment of the disclosure, the eardrum is identified, wherein determining a condition comprises determining a healthy eardrum in case the spectral composition exhibits a specific minimum amount of blue spectral components. A specific minimum amount of blue colors or UV components may be evaluated as an indication for an eardrum which does not exhibit any widened capillaries.

According to one embodiment of the disclosure, the eardrum is identified, wherein determining a condition comprises determining an unhealthy eardrum in case the spectral composition exhibits a specific maximum amount of blue spectral components, especially in dependence on a specific minimum amount of red spectral components. A specific maximum amount of blue colors or UV components may be evaluated as an indication for an eardrum which exhibits widened capillaries.

According to one embodiment of the disclosure, the eardrum is identified, and wherein the method further comprises a step of providing an index to a user in dependence on the spectral composition of the at least one captured image, especially an inflammation index indicating a likelihood of inflammation of the eardrum, especially in case an amount of blue spectral components does not exceed a specific minimum amount. In other words: If blue spectral components can only be identified to a relatively low degree or cannot be identified at all, then, it is concluded that the likelihood of inflammation of the eardrum is high.

According to one embodiment of the disclosure, the method further comprises providing an inflammation index to a user, indicating a likelihood of inflammation of the eardrum.

According to one embodiment of the disclosure, the eardrum is identified based on spectral information which is determined with respect to Rayleigh scattering. Rayleigh scattering may be evoked by few corpuscular components or cell layers in conjunction with (optical) transparency, which may be evaluated as an indicator for the eardrum. Evaluating/Acquiring spectral information with respect to the characteristics/particularities of Rayleigh scattering may improve accuracy of distinguishing the eardrum from other objects within the ear canal.

At least one of the above mentioned objects is also attained by a method of identifying the eardrum in a subject's ear, comprising the steps:

(S3) determining spectral information of radiation reflected within the ear canal of the subject's ear in order to automatically identify the eardrum; and (S4) identifying the eardrum in dependence on a specific amount of blue components and/or UV components detected within the reflected radiation. In other words: Determining spectral information may be carried out directly with respect to reflected radiation, irrespective of any manner/method of image analysis.

At least one of the above mentioned objects is also attained by a method of identifying a healthy eardrum in a subject's ear, comprising the steps:

(S2) capturing at least one image of the eardrum by means of an electronic imaging unit (40), especially based on reflected radiation of radiation emitted by at least one source of radiation;

(S3) determining spectral information in order to automatically identify the eardrum shown in the at least one image by electronic and/or optic means (44), especially by a logic unit;

(S4) identifying the eardrum in dependence on a specific amount of blue components and/or UV components of the image or of radiation reflected from the eardrum; and (S5a) determining the eardrum as being a healthy eardrum in dependence on a spectral composition which exhibits a specific minimum amount of blue spectral components or spectral components having wavelengths shorter than 550 nm, preferably shorter than 480 nm. Such a method allows for automatically carrying out diagnosis, or at least pre-diagnosis. In particular, the method allows for providing a user with a risk index. In addition, any more advanced or final disease diagnosis may be carried out by a physician.

At least one of the above mentioned objects is also attained by a method of identifying an inflamed eardrum in a subject's ear, comprising the steps:

(S2) capturing at least one image of the eardrum by means of an electronic imaging unit (40), especially based on reflected radiation of radiation emitted by at least one source of radiation;

(S3) determining spectral information in order to automatically identify the eardrum shown in the at least one image by electronic and/or optic means (44), especially by a logic unit;

(S4) identifying the eardrum in dependence on a specific amount of blue components and/or UV components of the image or of radiation reflected from the eardrum; and (S5b) determining the eardrum as being an inflamed eardrum in dependence on a spectral composition which exhibits a specific minimum amount of red spectral components or spectral components having wavelengths longer than 550 nm and/or a specific maximum amount of blue spectral components or spectral components having wavelengths shorter than 550 nm, preferably shorter than 480 nm. Such a method allows for automatically carrying out diagnosis, or at least pre-diagnosis. In particular, the method allows for providing a user with a risk index. In addition, any more advanced or final disease diagnosis may be carried out by a physician.

BRIEF DESCRIPTION OF THE SEVERAL VIEWS OF THE DRAWINGS

In the following figures, the present disclosure is described by way of examples, wherein FIG. 1 schematically shows an otoscope device according to a first embodiment of the disclosure, wherein the otoscope device is introduced in an ear canal as far as a position from which the otoscope device is enabled to "look around the corner".

In case any reference sign is not explicitly described in a respective figure, it is referred to the other figures. In other words: Like reference characters refer to the same parts or the same type or group of device throughout the different views.

DETAILED DESCRIPTION

Figure 1:
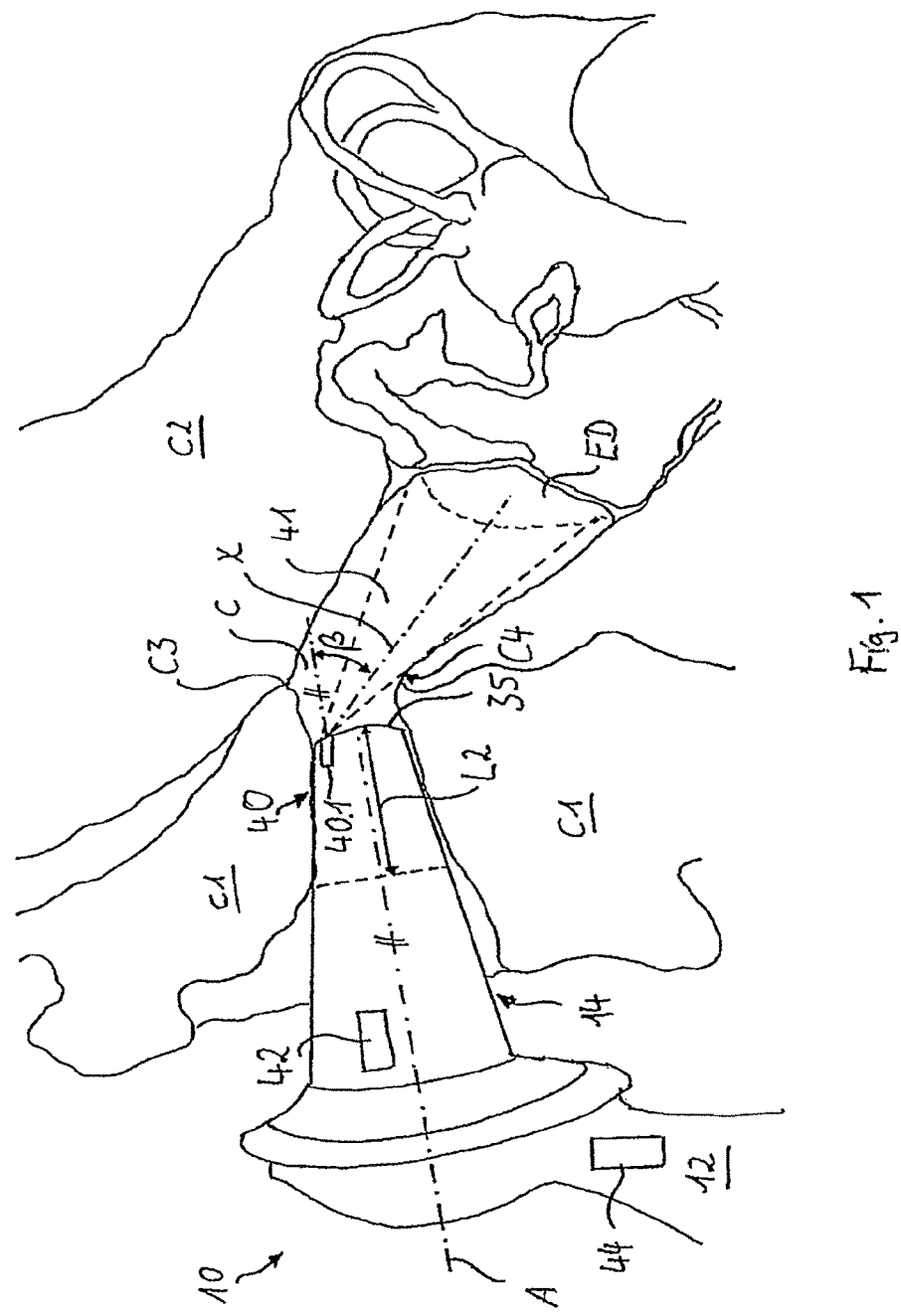

In FIG. 1, an otoscope 10 with a handle portion 12 and a head portion 14 including an electronic imaging 40 unit comprising a camera 40.1 is shown, wherein the camera 40.1 is positioned eccentrically (i.e., radially offset) with respect to a longitudinal axis A of the head portion 14. The camera 40.1 is positioned at a distal tip 35 of the head portion 14. The eccentricity (the radial offset) is, e.g., in the range of 1.5 mm to 2 mm. The head portion 14 is introduced into the ear canal C, and the outer surface of the head portion 14 or a probe cover (not shown) is in contact with soft connective tissue C1 surrounding the ear canal. In contrast to a hard bone section C2 of the ear canal, the soft connective tissue C1 is elastic and can be widened by the head portion 14. The camera 40.1 is in visual contact with the eardrum ED.

In a central section, the head portion 14 has a specific diameter, especially at an axial position defined by a specific length L2 which is preferably in the range of 28 mm to 32 mm, especially 20 mm. Along the length L2, the head portion 14 may exhibit a conical shape. The specific length L2 can be defined as the length along which the head portion 14 may be in contact with the patient's tissue, especially with the soft connective tissue C1 confining the outer ear canal, at least partially. The specific length L2 is preferably in the range of 18 mm to 22 mm, especially 20 mm. The diameter of the distal tip 35 is preferably in the range of 4.7 mm to 5.2 mm, more preferably 4.8 mm to 5 mm, especially 4.9 mm. A diameter at a middle portion of the head portion 14, especially at a distance of 20 mm from the distal tip 35, is preferably in the range of 8 mm to 9 mm, especially 8.5 mm.

The otoscope 10 is introduced within the ear canal C nearly as far as a curvature C4, i.e., nearly as far as a transition area C3 between the soft connective tissue C1 and the hard bone section C2. It is not required introducing the otoscope 10 any further/deeper. In the position shown in FIG. 1, the otoscope 10 is able to "look around the corner", in order to scan the eardrum ED. For this purpose, the camera 40.1 is arranged radially offset. The "corner" can be defined as the curvature C4 of the ear canal C.

The camera 40.1 has a field of vision 41 which is preferably conical. Geometrically, the field of vision 41 can be describes as a conus with an opening angle in the range of at least 80°, preferably of at least 110°, e.g., 120°. The camera 40.1 preferably is a wide angle color video camera. An optical axis X of the camera 40.1 is arranged (tilted) at an angle β with respect to the longitudinal axis, allowing the device to "look around the corner" more effectively. The angle β preferably is in the range of 20° to 40°.

The otoscope 10 exhibits electronic and/or optic means 44 which are in communication with the camera 40.1, e.g., by wire or wireless. The electronic and/or optic means 44 may be arranged at/in the handle portion 12 and/or at/in the head portion 14. The electronic and/or optic means 44 are configured for determining spectral information or for spectral analysis of images (or pixels of a respective image, or specific image sections) captured by the camera 40.1. The electronic and/or optic means 44 may be connected to at least one source of radiation 42, especially a light source, which may be arranged at/in the handle portion 12 and/or at/in the head portion 14. In particular, the source of radiation 42 may be arranged at the distal tip of the head portion 14, at least partially. The source of radiation 42 may comprise at least one LED (especially an LED of cold white color or blue color) and also at least one light guide. The electronic and/or optic means 44 may be configured to control the source of radiation 42, especially to adjust an intensity of radiation/illumination.

Figure 2:
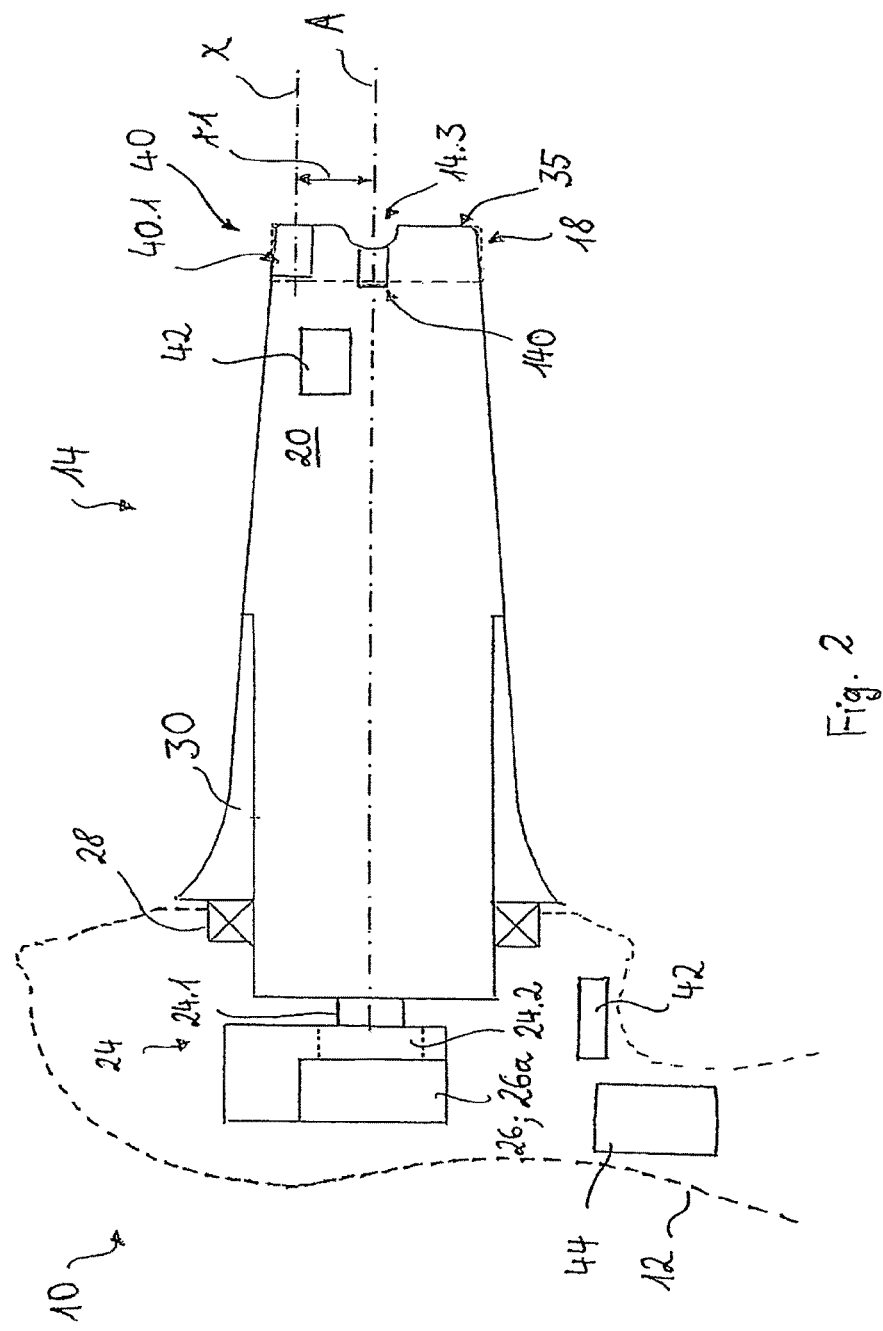
FIG. 2 schematically shows an otoscope device according to a second embodiment of the disclosure, wherein the otoscope device exhibits a plurality of technical features which facilitate its use, even by laypersons.

FIG. 2 shows an otoscope 10 with a handle portion 12 and a head portion 14. The head portion 14 has a distal end 18 including a distal tip 35, wherein the distal end 18 has a conical shape or a cylindrical shape (as indicated by the dashed line). An infrared sensor unit 140 is positioned centrically at the distal end 18. This position is only illustrated as an example. The distal end 18 may be provided with an indentation 14.3 for accommodating a reservoir portion of a probe cover (not shown). At the head portion 14, an electronic imaging unit 40 is provided, including a camera 40.1 having an optical axis X which is arranged radially offset with respect to a longitudinal axis A of the head portion 14, wherein the radial offset r1 of the optical axis X preferably is in a range between 1.5 mm and 2 mm. The camera 40.1 is arranged adjacent to an inner lateral surface of the distal end 18.

The otoscope 10 exhibits electronic and/or optic means 44, and may also exhibit a source of radiation 42. In context with the electronic and/or optic means 44 and the source of radiation 42, it is referred to the description of FIG. 1.

In order to position the camera 40.1 in a favorable position for capturing an image of the eardrum, the head portion may further include a movable portion 20 and a support structure 30. The movable portion 20 can be rotated by a motion mechanism 24 which is arranged in the handle portion 12. The movable portion 20 can be rotated with respect to the support structure 30. The motion mechanism 24 includes a drive shaft 24.1 which connects the movable portion 20 with the handle portion 12. The motion mechanism 24 includes a motor 26, especially a brushless motor 26a, which is connected to the drive shaft 24.1. Optionally, a gear 24.2 may be provided between the motor 26a and the drive shaft 24.1. The movable portion 20 is supported by a bearing 28 which is supported by the handle portion 12. The support structure 30 is supported by the handle portion 12. The support structure 30 provides a portion of the outer lateral surface of the head portion 14. The support structure 30 is fixed at the handle portion 12 by means of the bearing 28.

The otoscope 10 shown in FIG. 2 allows for simplified application by laypersons. The camera 40.1 be positioned in a favorable eccentric position automatically, unit the camera is in visual contact with the eardrum. The otoscope 10 shown in FIG. 2 even allows for application by the same person whose ear has to be scanned (e.g., a person living alone). The otoscope 10 shown in FIG. 2 even allows for a first (pre-) diagnosis without any assistance. The technical features of the otoscope shown in FIG. 1 may be combined with the technical features of the otoscope shown in FIG. 2.

Figure 3:
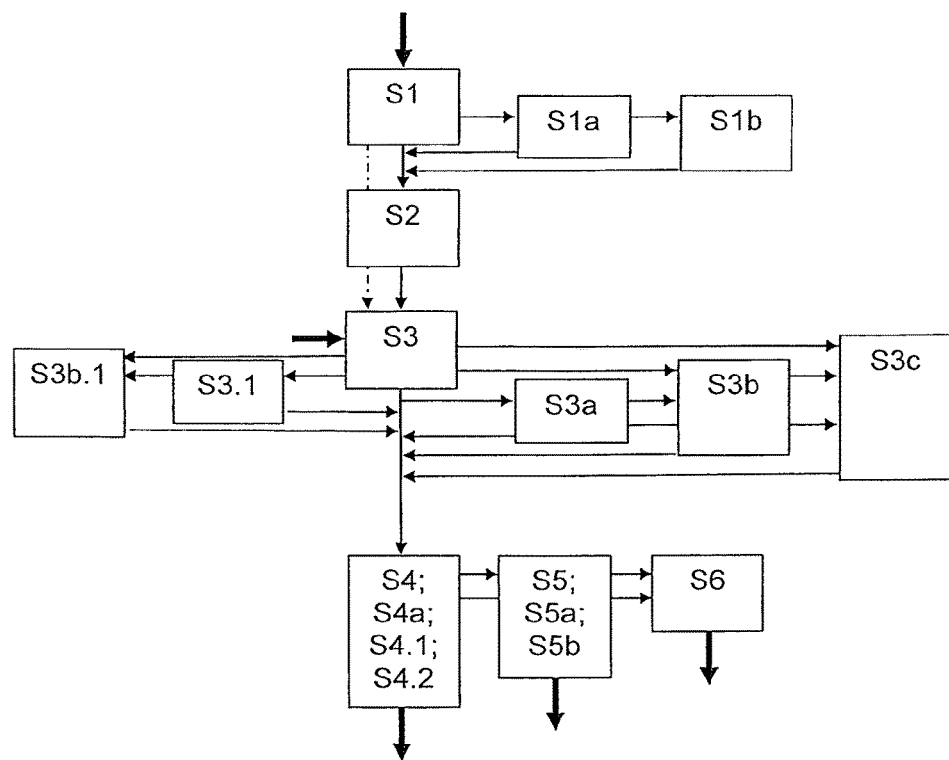
FIG. 3 schematically shows a flow chart of several methods of identifying and/or locating objects in a subject's ear according to embodiments of the present disclosure.

FIG. 3 shows a flow chart of examples of methods of identifying and determining objects. The respective method starts with a first step S1 of providing an electronic imaging unit, especially by introducing the electronic imaging unit into an ear canal of a subject's outer ear. In particular, the electronic imaging unit may comprise a camera which is arranged at a distal tip of a head portion of an otoscope. Alternatively, the respective method may directly start at step S3.

The step S1 may comprise a step S1a of introducing at least one source of radiation into the ear canal. Alternatively or in addition, the step S1 may comprise a step S1b of radiating, especially illuminating the ear canal. In a subsequent step S2, at least one image may be captured. In a subsequent step S3 (or, alternatively, as a first step), spectral information is determined, in order to identify objects. The step S3 may comprise a step S3a of determining spectral information based on a ratio of wavelengths (ratio of wavelengths of a specific range with respect to wavelengths of another specific range). Alternatively or in addition, the step S3 may comprise a step S3b of determining spectral information based on an intensity of radiation or based on brightness. Alternatively or in addition, the step S3 may comprise a step S3c of determining spectral information with respect to a specific image section. As indicated in FIG. 3, the steps S3a, S3b, S3c may be carried out independently from each other. In a subsequent step S4, at least one object is identified, especially the eardrum, in dependence on a specific amount of blue components and/or UV components of the image or of radiation reflected from the object. The at least one object may be identified in dependence on a spectral composition which exhibits a specific minimum amount of specific spectral components, especially a specific minimum amount of blue spectral components. The step S4 may comprise a step S4a of providing information to a user indicating that the eardrum has been identified and/or that the otoscope has been placed/introduced correctly within the ear canal. In other words: Based on the analysis of spectral components, especially blue components, the otoscope may automatically assess if the eardrum is visible, and if a layperson or physician has introduced the otoscope correctly. Therefore, the step S4a may allow for minimizing any risk of (accidental) misuse or any risk of misdiagnosis.

In a subsequent step S5, a condition, especially a medical condition, of the at least one object may be determined. In this step, a layperson may be provided with information which facilitates assessing any need of consulting/visiting a physician. In particular, it has been found that a spectral composition which differs from a specific spectral composition within the range of blue color or UV radiation may potentially indicate inflammation of the eardrum. An inflamed eardrum exhibits a reduced amount of blue tissue components, or does only reflect a reduced amount of blue or UV radiation, or does not reflect any blue or UV radiation at all. Determining the spectral composition of reflections of the eardrum may help the layperson to decide as to whether a physician should be visited or not. Any more advanced or final disease diagnosis may be carried out by the physician, e.g., on the basis of other symptoms exhibited by the subject, which are observed by the physician, or by the physician's further examination. Disease diagnosis may therefore not be derived from the output provided by embodiments of methods according to the disclosure. Acquired information is based on spectral analysis of the image and/or reflected radiation. Determining the degree/amount/ratio/percentage of blue components, especially a specific minimum amount of blue components, may help the layperson to decide not to visit a physician. Nonetheless, step S4 and/or step S5 may not only assist a layperson, but also a physician. In other words: step S5 may allow for minimizing any risk of misdiagnosis and for providing a hint about an infection/inflammation risk.

The step S5 may comprise a step S5a of determining a healthy eardrum in case the spectral composition exhibits a specific minimum amount of blue spectral components, and/or a step S5b of determining an unhealthy eardrum in case the spectral composition exhibits a specific minimum amount of red spectral components and/or a specific maximum amount of blue spectral components. The steps S5a and S5b may allow for further minimizing any risk of misdiagnosis, be it in context with use by a layperson or by a physician.

In a step S6 subsequent to step S4 or S5, a user may be provided with an index in dependence on the spectral composition of the at least one captured image, e.g., an inflammation index. An inflammation index may contain information about a healthy eardrum also. In particular, the inflammation index may be a low value (e.g., a value in the range of 1 to 3 of a scale from 1 to 10) in case there is a high amount of blue spectral components, especially in combination with a low amount of red spectral components.

The steps S3, S4, S5 and/or S6 may respectively be carried out by comparing the spectral information of the at least one image with spectral norm curves or with specific (predetermined) values of specific spectral components of the eardrum, respectively. Preferably, the spectral norm curves or specific (normalized) values refer to the UV spectrum and/or the spectrum of light, especially blue light.

Figure 4:
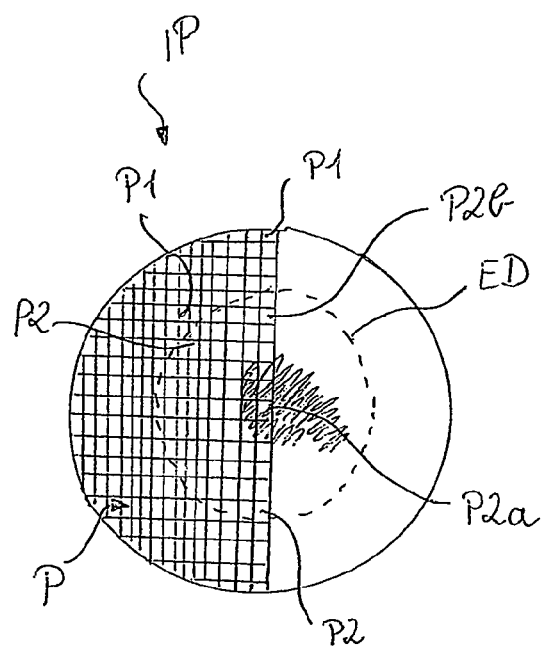
FIG. 4 schematically shows an acquired image composed of a plurality of pixels, wherein some of the pixels show a portion of the eardrum.

In FIG. 4, an acquired image IP composed of a plurality of pixels P is schematically shown. The image IP is composed of pixels P1 characterizing an object or part of the ear canal different than the eardrum, and pixels P2 characterizing the eardrum. The pixels P2 exhibit a ratio of spectral components in the spectrum below 480 nm to 500 nm to spectral components in the spectrum above 480 nm to 500 nm which is higher than the respective ratio of the pixels P1. The pixels P2 refer to both pixels P2a characterizing an inflamed part of the eardrum and pixels P2b characterizing a part of the eardrum which is not inflamed.

In particular, the respective ratio of the pixels P2a is higher than the ratio of pixels P1. In other words: Even in case the inflamed eardrum ED, the eardrum ED may be located and characterized based on the spectral ratio, especially a blue to green and/or blue to red ratio.

LIST OF REFERENCE SIGNS 10 otoscope device
12 handle portion
14 head portion
14.3 indentation
18 distal end
24 motion mechanism
24.1 drive shaft
24.2 gear
26 motor
26a brushless motor
28 bearing
30 support structure
35 distal tip
40 electronic imaging unit
40.1 camera
41 field of vision
42 source of radiation, especially light source
44 electronic and/or optic means, especially logic unit
140 infrared sensor unit
A longitudinal axis
C ear canal
C1 soft tissue
C2 hard bone
C3 transition area
C4 curvature
ED ear drum
IP acquired image composed of a plurality of pixels
L2 specific length
P pixel
P1 pixel characterizing an object or part of the ear canal different than the eardrum
P2 pixel characterizing the eardrum
P2a pixel characterizing an inflamed part of the eardrum
P2b pixel characterizing a part of the eardrum which is not inflamed
r1 radial offset
X visual axis, especially optical axis
β tilt angle
S1 step of providing an electronic imaging unit
S1a step of introducing at least one source of radiation
S1b step of radiating the ear canal
S2 step of capturing at least one image
S3 step of determining spectral information to identify objects
S3a step of determining spectral information based on a ratio of wavelengths
S3b step of determining spectral information based on an intensity of radiation or based on brightness
S3c step of determining spectral information with respect to a specific image section
S4 step of identifying at least one of the objects
S4a step of providing information to a user indicating that the eardrum has been identified and/or that the otoscope has been placed/introduced correctly within the ear canal
S5 step of determining a condition, especially a medical condition, of the at least one object
S5a step of determining a healthy eardrum in case the spectral composition exhibits a specific minimum amount of blue spectral components
S5b step of determining an unhealthy eardrum in case the spectral composition exhibits a specific minimum amount of red spectral components
S6 step of providing an index to a user in dependence on the spectral composition of the at least one captured image The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method of automatically identifying or locating an eardrum in a subject's outer ear, by means of an otoscope device, comprising the steps:
providing an otoscope including:
  a head portion configured to be introduced in an ear canal of the subject's outer ear, the head portion including an electronic imaging unit operable to capture at least one image of the subject's outer ear including the eardrum;
  an electronic and/or optic processing unit operable to determine spectral information; and
  at least one source of radiation connected to and controlled by the electronic and/or optic processing unit, the at least one source of radiation configured for emitting blue light and/or UV radiation;
introducing the head portion including the electronic imaging unit into the ear canal of the subject's outer ear;
introducing the at least one source of radiation into the ear canal and radiating the ear canal by means of the at least one source of radiation;
capturing at least one image of the subject's outer ear including the eardrum, by means of the electronic imaging unit, based on reflected radiation of radiation emitted by the at least one source of radiation;
determining and analyzing spatially resolved spectral information by means of the electronic and/or optic processing unit; and
automatically identifying or locating the eardrum by means of the electronic and/or optic processing unit in the at least one image by distinguishing the eardrum from surrounding tissue based on a specific amount of blue components and/or UV components within the at least one image of the subject's outer ear.

2. The method of claim 1, wherein the spatially resolved spectral information is determined based on a ratio of wavelengths shorter than 500 nm or 480 nm to wavelengths longer than 550 nm or 600 nm, and wherein the ratio is evaluated as an indicator for the eardrum and wherein the spectral information is determined based on brightness of the at least one image or a pixel or pixel area of the at least one image in dependence on a specific intensity of radiation of emitted and/or reflected radiation.

3. The method of claim 2, wherein a high ratio is evaluated as an indicator for a healthy eardrum.

4. The method of claim 1, wherein the automatically identifying or locating the eardrum depends on a specific intensity or ratio of blue spectral components and/or UV spectral components.

5. The method of claim 4, wherein the specific intensity or ratio of blue spectral components and/or UV spectral components is with respect to an amount of spectral components having wavelengths longer than 480 nm or 500 nm.

6. The method of claim 1, wherein the blue light and/or UV radiation is in the range of 550 nm to 10 nm.

7. The method of claim 6, wherein the blue light and/or UV radiation is below 480 nm.

8. The method of claim 1, wherein the electronic and/or optic processing unit is configured for adjusting a spectral composition of radiation emitted by the at least one source of radiation.

9. The method of claim 8, wherein the spectral composition of radiation is with respect to a specific wavelength below 550 nm.

10. The method of claim 9, wherein the spectral composition of radiation is with respect to a specific wavelength below 480 nm.

11. The method of claim 8, wherein the spectral composition of radiation is with respect to a specific maximum within the spectrum of 380 nm to 500 nm.

12. The method of claim 11, wherein the spectral composition of radiation is with respect to a specific maximum within the spectrum of 420 nm to 480 nm.

13. The method of claim 8, wherein the electronic and/or optic processing unit is configured for calibration of the spectral composition of radiation emitted by the at least one source of radiation, and for comparing a determined spectral composition of reflected radiation with the calibrated spectral composition of emitted radiation.

14. The method of claim 1, wherein the electronic and/or optic processing unit is configured for adjusting an intensity of radiation of the at least one source of radiation.

15. The method of claim 14, further comprising adjusting the intensity of radiation to a minimum intensity for acquiring the at least one image.

16. The method of claim 15, further comprising reducing the intensity of radiation in case the at least one image exhibits a spectral composition which exceeds a specific maximum amount of red spectral components.

17. The method of claim 1, wherein determining spectral information comprises analysis of blue spectral components, and wherein identifying the eardrum is carried out in dependence on the amount of blue spectral components relative to the amount of red spectral components.

18. The method of claim 1, wherein determining spectral information comprises pixelwise subtraction of red spectral components.

19. The method of claim 1, wherein the method further comprises a step of determining a medical condition of the eardrum in dependence on a spectral composition which exhibits a specific minimum or maximum amount of specific spectral components.

20. The method of claim 19, wherein determining a medical condition comprises determining a healthy eardrum in case the spectral composition exhibits a specific minimum amount of blue spectral components, or wherein determining a medical condition comprises determining an unhealthy eardrum in case the spectral composition exhibits a specific maximum amount of blue spectral components in dependence on a specific minimum amount of red spectral components.

21. The method of claim 1, wherein the eardrum is identified based on spectral information which is determined with respect to Rayleigh scattering.

22. A method of automatically identifying or locating an eardrum in a subject's outer ear, by means of an otoscope device, comprising the steps:
providing an otoscope including:
a head portion configured to be introduced in an ear canal of the subject's outer ear;
an electronic and/or optic processing unit operable to determine spectral information; and
at least one source of radiation connected to and controlled by the electronic and/or optic processing unit, the at least one source of radiation configured for emitting blue light and/or UV radiation;
introducing the head portion into the ear canal of the subject's outer ear;
introducing the at least one source of radiation into the ear canal and radiating the ear canal by means of the at least one source of radiation;
determining and analyzing spectral information of reflected radiation by means of the electronic and/or optic processing unit; and
automatically identifying or locating the eardrum by distinguishing the eardrum from surrounding tissue based on a specific amount of blue components and/or UV components of the reflected radiation from the subject's outer ear.

23. The method of claim 22, wherein the spectral information of reflected radiation is determined based on a ratio of radiation in the spectrum below 480 nm to 500 nm to radiation in the spectrum above 480 nm to 500 nm.

24. The method of claim 23, wherein the spectral information of reflected radiation is determined based on a specific intensity of the reflected radiation within the spectrum of blue light and/or UV radiation.

25. A method of automatically identifying a healthy eardrum in a subject's ear, comprising the steps:
capturing at least one image of the subject's ear by means of an electronic imaging unit;
determining spectral information by an electronic and/or optic processing unit;
automatically identifying an eardrum shown in the at least one image by the electronic and/or optic processing unit in dependence on a specific amount of blue components and/or UV components of the image of the subject's ear; and
automatically determining the eardrum as being a healthy eardrum in dependence on a spectral composition which exhibits a specific minimum amount of blue spectral components or spectral components having wavelengths shorter than 550 nm or 480 nm.

26. A method of automatically identifying an inflamed eardrum in a subject's ear, comprising the steps:

capturing at least one image of the subject's ear by means of an electronic imaging unit;

determining spectral information by means of the electronic and/or optic processing unit;

automatically identifying the eardrum shown in the at least one image by electronic and/or optic processing unit;

identifying the eardrum in dependence on a specific amount of blue components and/or UV components of the image or of radiation reflected from the eardrum; and determining the eardrum as being an inflamed eardrum in dependence on a spectral composition which exhibits a specific minimum amount of red spectral components or spectral components having wavelengths longer than 550 nm and/or a specific maximum amount of blue spectral components or spectral components having wavelengths shorter than 550 nm or 480 nm.

* * * * *